United States Patent [19]

Robillard

[11] 4,434,025

[45] Feb. 28, 1984

[54] CONTROLLING CRYSTALLINITY AND THICKNESS OF MONOCRYSTALLINE LAYER BY USE OF AN ELLIPTICALLY POLARIZED BEAM OF LIGHT

[76] Inventor: Jean J. Robillard, 46 Arnold Rd., Pelham, Mass. 01002

[21] Appl. No.: 270,242

[22] Filed: Jun. 4, 1981

[51] Int. Cl.³ .............................................. C30B 23/02
[52] U.S. Cl. ..................................... 156/601; 156/605
[58] Field of Search ....................... 156/601, 605, 613; 427/86, 85; 148/171, 175, 188; 252/62.3 GA, 62.3 ZB

[56] References Cited

U.S. PATENT DOCUMENTS

| 3,718,502 | 2/1973 | Gibbons | 156/605 |
| 3,892,490 | 7/1975 | Uetsuki et al. | 156/601 |
| 4,203,799 | 5/1980 | Sugawara | 156/601 |

*Primary Examiner*—Hiram H. Bernstein
*Attorney, Agent, or Firm*—Sherman & Shalloway

[57] ABSTRACT

Monocrystalline layers of semiconductor materials are formed by epitaxial growth from thermal vapor deposition. Crystallinity and thickness of the monocrystalline layers are monitored and controlled during growth by ellipsometry. Low defect density thin film monocrystalline semiconductor devices with appropriate doping levels are formed. These are useful in photovoltaic solar cells of high efficiencies which can approach the theoretical limits.

10 Claims, 15 Drawing Figures

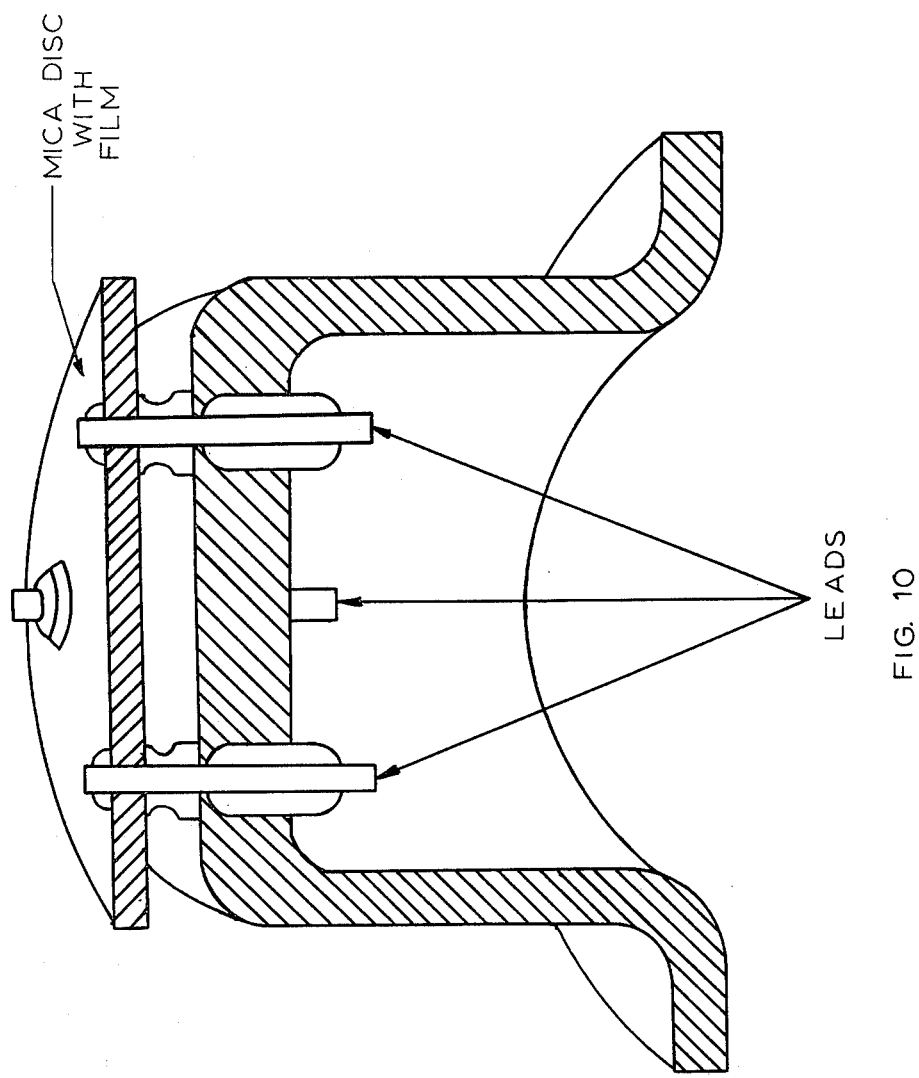

CONTROLLING CRYSTALLINITY AND THICKNESS OF MONOCRYSTALLINE LAYER BY USE OF AN ELLIPTICALLY POLARIZED BEAM OF LIGHT

FIELD OF THE INVENTION

This invention relates to a method of preparing thin film high efficiency solar cells by epitaxial growth from the vapor phase. More particularly, this invention provides a vapor deposition process for providing low defect density epitaxial growth of monocrystalline films by continuously monitoring the crystallinity, stoichiometry and thickness of the growing film layer.

DISCUSSION OF THE PRIOR ART

Photovoltaic solar cells can be made in a variety of ways. A general classification is not simple but must take into account such factors as the composition, structure, geometry of the cells as well as their method of preparation.

The photovoltaic effect arises from the existence of a potential barrier at a junction between two semiconductors or between two regions of a semiconductor differently doped. Asymmetrical photogeneration of electrons and holes on each side of the barrier provides a source of power which can be dissipated in an external load.

The choice of a material for high efficiency solar cells depends on many parameters, the most important being the band gap. The theoretical efficiency versus band gap emphasizes the value of Group III-V compounds such as GaAs and CdTe. Other factors that are relevant include the absorption edge of the material and its position in the spectral distribution of the solar energy. Also of concern is the relation that must exist between the energy gap of the semiconductor and the load impedance for maximum power transfer from the cell. All these parameters and many others have to be considered in the choice of the material for solar cells.

The starting material for the preparation of solar cells can be in the form of a powder or bulk material.

When a powder is used it is agglomerated by sintering or dispersed in a binder to form a film on a conductive base. The location of the junction can be at the surface of each individual grain or at the interface between the film and the conductive base. Materials used in powder form for the manufacture of solar cells include CdS, CdTe, CuO, and some organic powders such as phthalocyanine. Cells made of powder material have relatively low efficiency (3 to 5%).

Bulk material can be either monocrystalline or polycrystalline Monocrystalline materials provide much higher efficiencies due to the lack of recombination of charge carriers at the crystal boundaries. The junction in polycrystalline materials is obtained generally by diffusion of doping material at appropriate temperature. In monocrystals, the junction is made by one of three methods:

Diffusion, as in polycrystalline materials
Homoepitaxy of one or several layers on the surface of the crystal
Heteroepitaxy of one or several layers on the surface of the crystal.

The growth of the epitaxial layers can be carried on by any one of the following techniques:
Chemical vapor deposition (CVD)
Liquid phase epitaxy (LPE)
Thermal vapor deposition (TVD)

In the CVD process a metal organic compound in the gas form, or carried by a gas carrier, is decomposed on the surface of the crystal and precipitates the metal on that surface thus forming the epitaxial film.

In liquid phase epitaxy the material of the epitaxial layer is melted and put in contact with the surface of the crystal while proper temperature gradients are set to provide the conditions for epitaxial growth.

In thermal vapor deposition the material is sublimed and condensed on the surface of the crystal. This technique has several advantages over either CVD or LPE, and epitaxial growth is preferred over diffusion.

For example, with regard to doping, the thermally evaporated layer structure has a definite advantage over the bulk structure prepared by diffusion or liquid epitaxy. This is due to the fact that in bulk crystals dopant migration and boundary diffusion takes place during the cooling cycle; this is necessarily slow due to the specific heat of the material and the necessity of avoiding heat gradients in order to maintain crystal perfection. Amphoteric impurities such as Si and Ge in GaAs can move from III to V position thereby changing the donor to acceptor nature of the doped crystal. Si generally occupies Ga sites resulting in a shallow donor state (0.005 eV below the conduction band). When a GaAlAs epitaxial layer forms on GaAs with Si as dopant, the latter has the tendency to replace As atoms resulting in a P type layer. This can be used to produce P-N junctions in the course of an epitaxial growth process.

Another important point in favor of thermal vapor growth is the dopant segregation occuring during all growth processes involving liquid-solid interface affecting the stoichiometry of the region close to that interface.

Crystal growth from vapor phase is free from migration of the lattice components or dopant as the stoichiometry is determined by the rate of evaporation of each constituent and does not vary during the growing process.

Epitaxy and Epitaxial Growth a. Introduction

Single crystal films can be built on other crystalline substrates through a two dimensional orientation exerted by the substrate onto the film. This is generally called epitaxy. In this process the periodic field produced by the two dimensional lattice of atoms at the surface of the crystalline substrate induces the positioning of corresponding atoms in the film. These positions correspond to the potential minima in the field. A perfect match is possible when the two components (film and substrate) are made of the same material (homoepitaxy). In that case the location of the atoms on either side of the interface is identical. If the materials are different (heteroepitaxy) the previous situation only exists if the two lattices at the interface have exactly the same dimension which is generally not the case and a certain disregistry (or misfit) will exist between the atoms at the interface. The misfit $\delta$ is defined as the quantity:

$$\delta = \Delta a / a_0$$

where: $\Delta a = a - a_0$, $a$ being the lattice constant of the film and $a_0$ that of the substrate. During the growth process the potential energies of the atoms in the film are reduced by displacements toward the potential minima and the forces acting on the arrangement show a threshold under which the registry is not possible. This threshold corresponds to a misfit:

$$\delta \leq 0.1$$

The displacements introduce stresses in the crystal which affect its electronic structure causing local field perturbations affecting the electronic properties of the crystal.

b Theories of epitaxy

Several theories of epitaxy have been suggested although none of them provide a completely satisfactory account of the observed facts.

G. Menzer, Naturwissenchaften, 26, 385 (1938) suggested that in a cubic structure the initial nuclei of the deposit grow with [111]planes and grow together to form an interpenetrating lattice which eventually develops into the parallel orientation.

O. G. Engel, J. Chem. Phys. 20, 1174 (1952) has put forward a theory in which the orientation depends on an ionization process between the atoms in presence and upon the misfit of the intermediate salt with both the substrate and the film.

In Van der Merve theory, Disc. Faraday Soc. 5, 201 (1949) it is assumed that the initial stage of growth of an oriented deposit is the formation of an unmobile monolayer of regular atomic pattern. This monolayer is considered to be homogeneously deformed to fit on to the substrate in order to form a two dimensional nucleus.

In general, it is found that the probability of achieving a good epitaxial film depends on 3 major factors:
good lattice match;
cleanliness of the substrate;
free energy (temperature) available at the surface of the substrate to provide enough mobility of the atoms for orientation.

The latter condition will determine a critical temperature called epitaxial temperature (Te) under which the arrangement cannot take place.

Deposition physics and crystal growth

In vacuum sublimation by the thermal vapor deposition technique the material of the film is heated in a special crucible at low pressure ($10^{-7}$ mm-Hg) and condenses on the substrate. If the proper conditions prevail an epitaxial layer can be formed. The atoms or molecules originating from the source material reach the surface of the substrate (monocrystal) where they form a two dimensional gas layer in which their mobility depends mostly on the substrate temperature. The gas layer is subjected to the periodic field of the crystal lattice and the trapping location of the atoms in the layer corresponding to potential minima in the field (see FIG. 1) at a distance of $a_0$ In order to reach such location the atoms have to cover an average distance of $a_0/2$. Consequently, the optimum condition for expitaxy are met when the mean free path $\lambda$ of the atoms in the two dimensional gas layer at the surface of the substrate is such that:

$$\lambda = a_0/2 \tag{1}$$

where $\lambda$ is given by the Kinetic Theory of Gases as equal to:

$$\lambda = \frac{0.707}{\pi \sigma^2 n} \tag{2}$$

where $\sigma$ is the diameter of the atom and n the number of atoms in the gas per cm$^2$. If, on the other hand, the two dimensional gas layer in formation is assumed to be in equilibrium with the gas arriving on the substrate surface one can apply the Clapeyron Helmotz equation and write:

$$L = RT^2 \frac{d}{dT} \text{Log}(P) \tag{3}$$

which gives by integration:

$$\text{Log}(P) = \int_0^T \frac{L}{RT^2} dT = -\frac{L}{RT} + C \tag{4}$$

or $$P = Ae^{-\frac{L}{RT}} \tag{5}$$

where:
L is the latent heat of sublimation
R is the universal gas constant
T is the temperature of the substrate
P is the gas pressure in the two dimensional layer on the substrate
C and A are integration constants.

Assuming that the solid gas phases are in equilibrium, the number of atoms $n_2$ leaving the epitaxial layer per cm$^2$ is equal to the number $n_1$ of atoms entering the same layer. This number:

$$n = n_1 = n_2 \tag{6}$$

is given by:

$$n = \frac{P}{\sqrt{2\pi mkt}} \tag{7}$$

and, using (5):

$$n = \frac{Ae^{-\frac{L}{RT}}}{\sqrt{2\pi mkt}} \tag{8}$$

which makes it possible to express $\lambda$ in (2) as:

$$\lambda = \frac{0.707 \sqrt{2\pi mkt}}{\pi \sigma^2 Ae^{-\frac{L}{RT}}} \tag{9}$$

or $$\lambda = K\sqrt{T} \, e^{\frac{L}{RT}} \tag{10}$$

with:

$$K = \frac{0.707 \sqrt{2\pi mk}}{\pi \sigma^2 A} \tag{11}$$

Various parameters of interest for materials generally useful for solar cell semiconductors are shown in Table 1.

TABLE I

| | Ga | As | Al | P | Ga As | Ga P | Al As | Ga Al As |
|---|---|---|---|---|---|---|---|---|
| m | 69.7 | 75 | 27 | 31 | 144.7 | 100.7 | 102 | 171.7 |
| $\sigma$ | 0.62 | 0.47 | 0.50 | 0.34 | 1.22 | 1.18 | 1.20 | 1.18 |
| A | 10.820 | 1034 | 17.77 | 25 | $8.4 \cdot 10^{-9}$ | $8.46 \cdot 10^{-10}$ | $2.4 \cdot 10^{-7}$ | $5.2 \cdot 10^{-11}$ |
| L | 52 | 54 | 55 | 48 | 20 | 17 | 23 | 15 |
| $T_e$ | 200 | 242 | 350 | 280 | 510 | 530 | 550 | 465 |
| $\lambda$ | 2.44 | 3.76 | 3 | 2.22 | 5.65 | 5.45 | 5.64 | 5.32 |
| K | $5.44 \cdot 10^{-27}$ | $1.03 \cdot 10^{-25}$ | $3.16 \cdot 10^{-24}$ | $5.2 \cdot 10^{-24}$ | $2.6 \cdot 10^{-15}$ | $2.3 \cdot 10^{-14}$ | $7.8 \cdot 10^{-16}$ | $5.6 \cdot 10^{-19}$ |

The epitaxial temperatures $T_e$ in Table 1 were obtained for $\lambda = a_0/2$ and are in good agreement with experimental data.

The maximum departure $\Delta T_e$ from the epitaxial temperature corresponds to the difference between $T_e$ and the temperature $T_{e+1}$ for which $\lambda \leq 3a_0/2$ or:

$$\Delta T_e = T_e - T_{e+1} \tag{12}$$

The physical meaning of $\Delta T_e$ is the difference between two situations, one corresponding to the conditions for having the maximum probability for trapping the atoms at the sites of lowest potential, which means giving them a mean free path at least equal to $a_0/2$ with a temperature $T_e$, and the other corresponding to the next most probable condition, i.e. a mean free path of $3a_0/2$ and a temperature of $T_{e+1}$. For GaAs $\Delta T_e$ is about 1° C.

The equilibrium conditions necessary for the growth of an epitaxial layer can be maintained with the substrate temperature up to several atomic layers. For thicker layers some energy has to be added to the upper layers. It has been found that such organization can be provided by intermittant electron bombardment of the surface during the growth and layers up to several microns can easily be maintained.

Film growth control

In general, the parameters related to the growth of thin monocrystalline films are the temperature, the thickness, the crystallinity and the rate of growth. A precise control of these parameters is necessary to insure a good homogeneity in the epitaxial layer.

An accurate measurement of the temperature at the location of the growth cannot be made directly as the presence of any measuring device in contact with the surface will perturb the growing process.

Generally an approximate measurement can be made with a thermocouple or a thermistor on the opposite side of the substrate by making the assumption that a thermal equilibrium is reached inside the epitaxial chamber. However, this is not exactly the case as the substrate is supported mechanically by metal parts which are heat conductive and provide a heat gradient at the edges of the substrate.

Also the lower aperture of the chamber for the introduction of the vapor is responsible for radiative heat exchange with the exterior.

The thickness can be evaluated indirectly with a quartz balance which is a quartz crystal over which a quantity of the material is evaporated concurrently with the vapor deposition in the epitaxial chamber. The damping of the crystal varies with the thickness of the layer deposited and the shift in frequency can be measured in an oscillator circuit driven by the quartz crystal. The shift in frequency can then be related to this thickness. One can also measure the thickness by optical interferometry when the thickness exceeds half wavelength of the radiation used for the measurement.

Crystallinity can be controlled by a variety of methods including electrical and optical measurements.

Optical measurements are of course preferred as they do not involve any physical contacts.

The rate of growth can be obtained by monitoring the thickness as a function of time.

To date, however, none of these optical or electrical techniques have proven entirely satisfactory in their ability to measure or control epitaxial growth of thin monocrystalline films. These known techniques are deficient in terms of accuracy, simplicity, response time and/or cost to provide solar cell semiconductor film structures which are sufficiently cost efficient or effective to allow solar cell technology to make a significant impact as an alternative energy source. Furthermore, none of these techniques can be used to simultaneously control crystallinity and measure thickness during the growth process.

Since monocrystalline film structures can theoretically provide the optimum energy conversion efficiency for solar cell photovoltaic devices it would clearly be highly advantageous to produce such monocrystalline film structures which approach the theoretically optimum efficiency. This has been accomplished by the process of the present invention which combines the advantages of the thermal vapor deposition technique for epitaxial film growth with a unique system for continuously controlling crystallinity and measuring the thickness of the growing monocrystalline film with appropriate feedback for controlling the parameters for epitaxial growth.

SUMMARY OF THE INVENTION

The present invention provides a process for forming thin monocrystalline film structures which can be used, for example, in solar photovoltaic cells. According to this process, the thickness and crystallinity of the epitaxial growth of the film on a preformed removable expitaxial substrate is continuously and rapidly (substantially instantaneously) measured and monitored whereby the parameters of epitaxial growth, particularly temperature are controlled by appropriate and necessary adjustment either manually, or preferably automatically. The optical measuring and monitoring system used in this invention which provides the feedback for controlling epitaxial growth is based on ellipsometry. Ellipsometry is a known technique for measuring thickness of thin amorphous films and is generally described in the literature, for example, see A. Rothen, Rev. Scient. Inst. 16, 26 (1945); R.J. Archer, J. Opt. Soc. Amer. 52, 970 (1962).

In ellipsometry an elliptically polarized beam of light is directed at a low angle of incidence over the surface of the epitaxial substrate where the monocrystalline film is growing. The reflected light is monitored with regard to the polarization and amplitude of the reflected beam of light. The differences between the values for the incident and reflected light provides the data for the measurement of the crystallinity and thickness of the film.

When the results are analyzed and show that a monocrystalline structure is not forming this information is fed back to the epitaxial substrate in terms of an increase or decrease in the temperature at the surface of the substrate whereby the mean free path of the impinging atoms or molecules is adjusted to provide the necessary mobility to assure proper orientation, i.e. satisfy equation (1) above. The thickness is also continuously monitored and analyzed and when the desired predetermined thickness is reached the path between the material source in the thermal vapor deposition system and the growing monocrystalline film is closed.

Furthermore, according to this invention when the epitaxial monocrystalline film of the first source material, i.e. semiconductor metal or compound or alloy, is completed a second and subsequent source materials can be provided and the process repeated to provide a multilayer thin film structure of two or more monocrystalline layers.

Still further, according to the invention process one or more of the formed thin film monocrystalline layers can be doped where necessary, by appropriate dopants by depositing an amorphous layer of the dopant on the monocrystalline layer. Preferably, the dopant is added after the last monocrystalline layer is formed and is allowed to diffuse throughout several or all of the monocrystalline layers.

BRIEF DESCRIPTION OF THE DRAWINGS

The invention will now be described in greater detail with regard to preferred embodiments thereof by reference to the following description and with the aid of the accompanying drawings in which:

FIGS. 10, 11, and 12 are illustrations of alternative solar cell structure incorporating the epitaxial semiconductor film of this invention.

DETAILED DESCRIPTION OF THE INVENTION AND PREFERRED EMBODIMENTS

Figure 1:
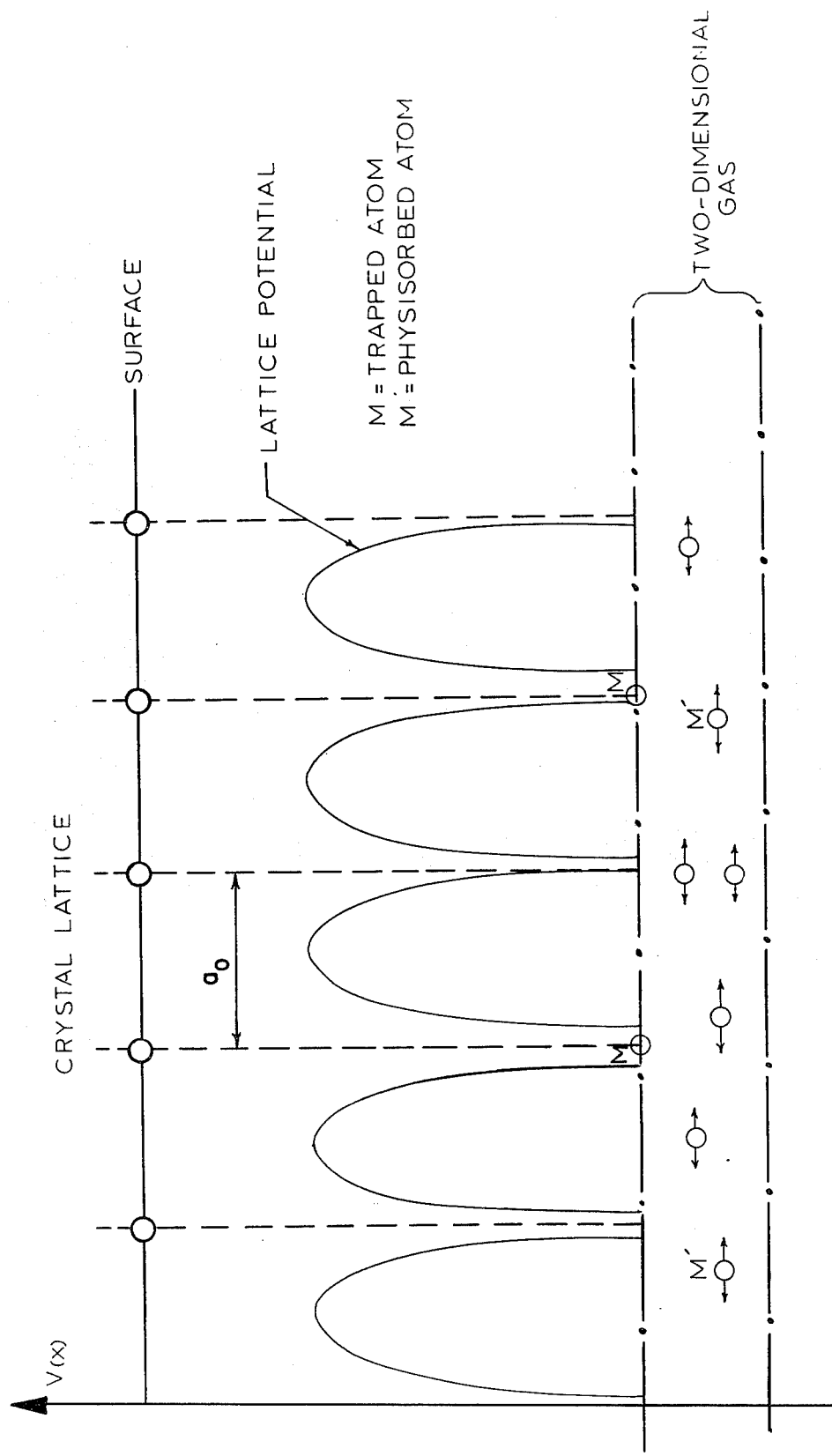
FIG. 1 is a schematic graphic illustration of the potential energy distribution in the two-dimensional gas in epitaxial growth by thermal vapor deposition.

The present invention provides single layer and multiple layer thin film monocrystalline semiconductor structures by combining thermal vapor deposition (TVD) technology to produce an atomic or molecular stream of high thermal energy together with an ellipsometric optical method of measuring and monitoring the epitaxial growth of one or several monocrystalline layers made from the material deposited by the atomic or molecular stream.

The combination of TVD with ellipsometric optical monitoring provides monocrystalline films having a low concentration of structural defects which is an essential condition for the manufacture of high efficiency photovoltaic cells. The atomic or molecular stream generated by TVD provides an accurate control of the deposition of the film forming material, with regard to quantity, direction and energy. The ellipsometric optical technique is a highly sensitive, rapid continuous measurement method for evaluating and measuring crystallinity and film thickness which allows measurement down to several Angstroms and with a precision of a few Angstroms.

Ellipsometry is the measurement of the effect of reflection on the state of polarization of polarized light. The state of polarization is characterized by the phase and amplitude relationship between two component plan waves of the electric field vector into which the polarized oscillation may be resolved. One wave P is in the plan of incidence. The other S is normal to the plan of incidence. Reflection causes a change in the relative phases of the P and S waves and a change in the ratio of their amplitudes. The angle $\Delta$ is the change in phase and the angle $\psi$ is the arc $t_g$ of the change in amplitude ratio.

The general relationship between $\Delta$ and $\psi$ can be numerically calculated as a function of several parameters, including the thickness d of the film, the index of refraction $n_1$ of the film, the index of refraction $\bar{n}$ of the substrate, and the angle of incidence $\phi$, by the equation given by R. J. Archer, J. Opt. Soc. Amer. 52, 970 (1962).

In practice, however, $\Delta$ and $\psi$ are experimentally measured during the growth of the crystal using optical ellipsometry equipment which has been modified so that the measurements can be made automatically. With such equipment the composition of the waves corresponding to $\Delta$ and $\psi$ can be displayed on a cathode ray tube and their signification in terms of thickness of the layer and crystallinity can be interpreted from that observation. The signal fed into the display can also be processed to generate proper feedback for an automatic control of the crystalline growth. The role of the ellipsometer is two-fold:

(a) to control the crystallinity of the growing layer, and (b) to measure its thickness.

The method is based on the variation in ellipticity of an elliptically polarized beam of light reflecting at low incidence over the substrate where the film is growing. If the film is monocrystalline, the reflected beam is also elliptically polarized and the difference in ellipticity with the reflection on the substrate is a measurement of its thickness. If the film is amorphous, the reflected beam is depolarized. If it is polycrystalline, the electric and magnetic vectors on the reflected beam will have as many components as there are crystallites in the cross-section of the beam on the reflective surface, thus rendering complex the polarization of the reflected beam.

Figure 2:
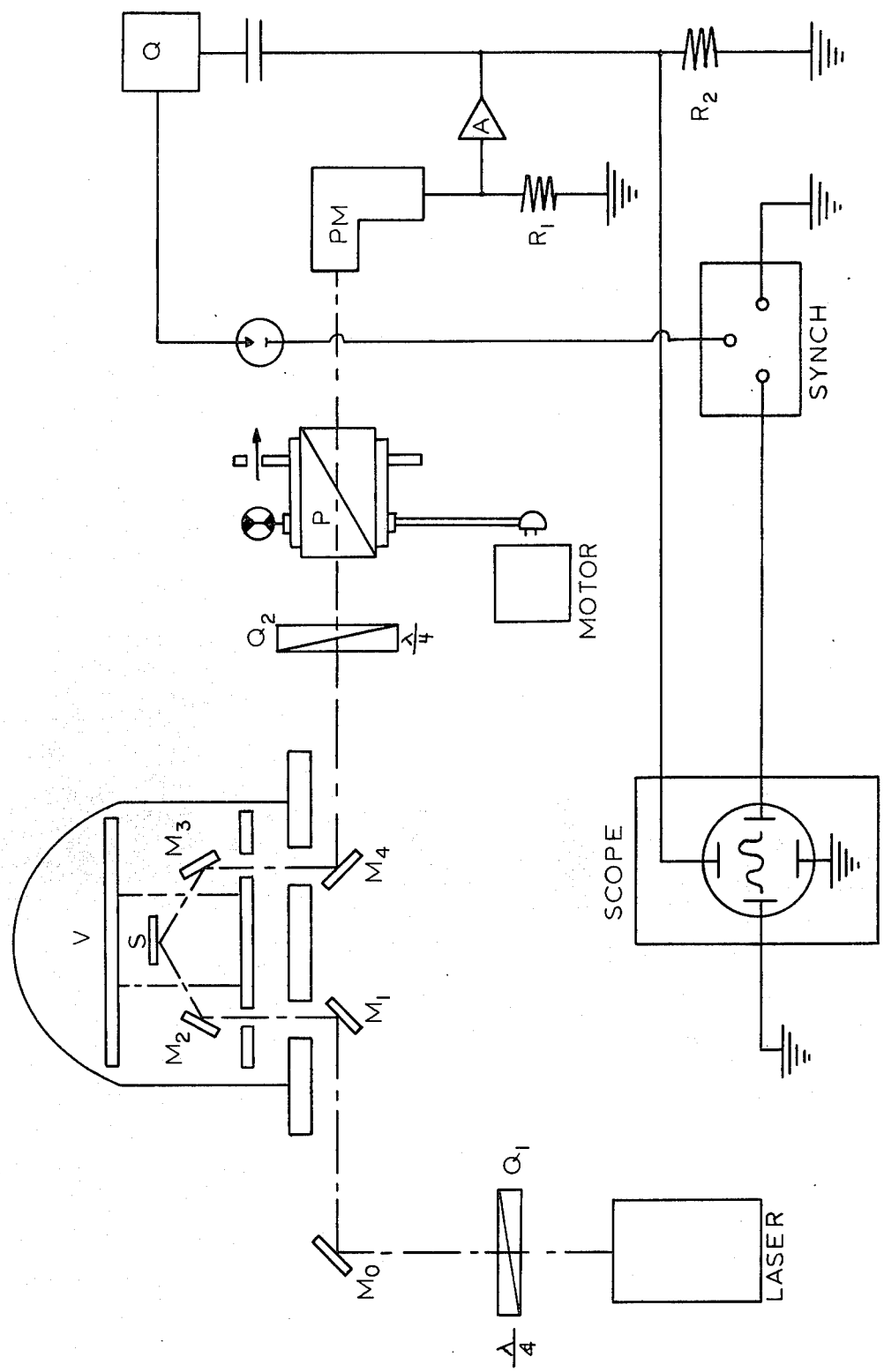
FIG. 2 is a schematic illustration of the ellipsometer system and thermal vapor deposition vacuum chamber used in the process of this invention.

An ellipsometer is made of two parts: the source and the analyzer. The source generally comprises a monochromatic light source, a collimator, a polarizer giving linearly polarized light with two components at right angles, and a quarter wave plate introducing a different phase delay for these two components, hence producing an elliptically polarized light. The analyzer is made of the same elements as the source in a symmetrical relationship, starting with the quarter wave plate converting the elliptical light into two components; a polarizer for the angular separation of these two components and a detector. Practically, the monochromatic light source, the collimator and the polarizer can all be replaced by a laser with a linearly polarized beam (FIG. 2). The detector can be a photomultiplier or a phototransistor, both adapted to the wavelength of the light being used.

For the monitoring of film growth in a vacuum chamber V both the source and the analyzer will be located externally. The elliptically polarized beam from the source will enter the chamber through a vacuum-tight optical window $W_1$ and then be guided to the substrate by a set of front surface mirrors $M_1$ and $M_2$. The reflected beam, equally guided by a set of mirrors $M_3$, $M_4$ will leave the chamber through another vacuum-tight optical window $W_2$ to reach the analyzer. The measurement of the ellipticity of the reflected beam is made automatically, since manual rotation of the polarizer and the quarter wave plates $Q_1$, $Q_2$ will be too slow for an efficient monitoring.

For this purpose, the polarizer is mounted on a rotatable bearing, preferably an air bearing, and is driven by a synchronous motor at the rate of about 3600 rpm's or more. It has been found convenient to display the amplitude of the light as a function of the angle of rotation of the polarizer. To achieve this, the H scanning of the oscilloscope is triggered by a signal produced by the passage of a hole at the periphery of a disc fastened to the polarizer between a pinlight and a photodiode. Under such circumstances, the signal issued from the photodetector and fed into the vertical amplifier of the oscilloscope produces a curve with two maxima on the screen for an angular rotation of $\pi$.

The scanning frequency being twice the frequency of rotation of the polarizer, the two maxima observed correspond to the two axes of the ellipse in the polarization plane.

Figure 3:
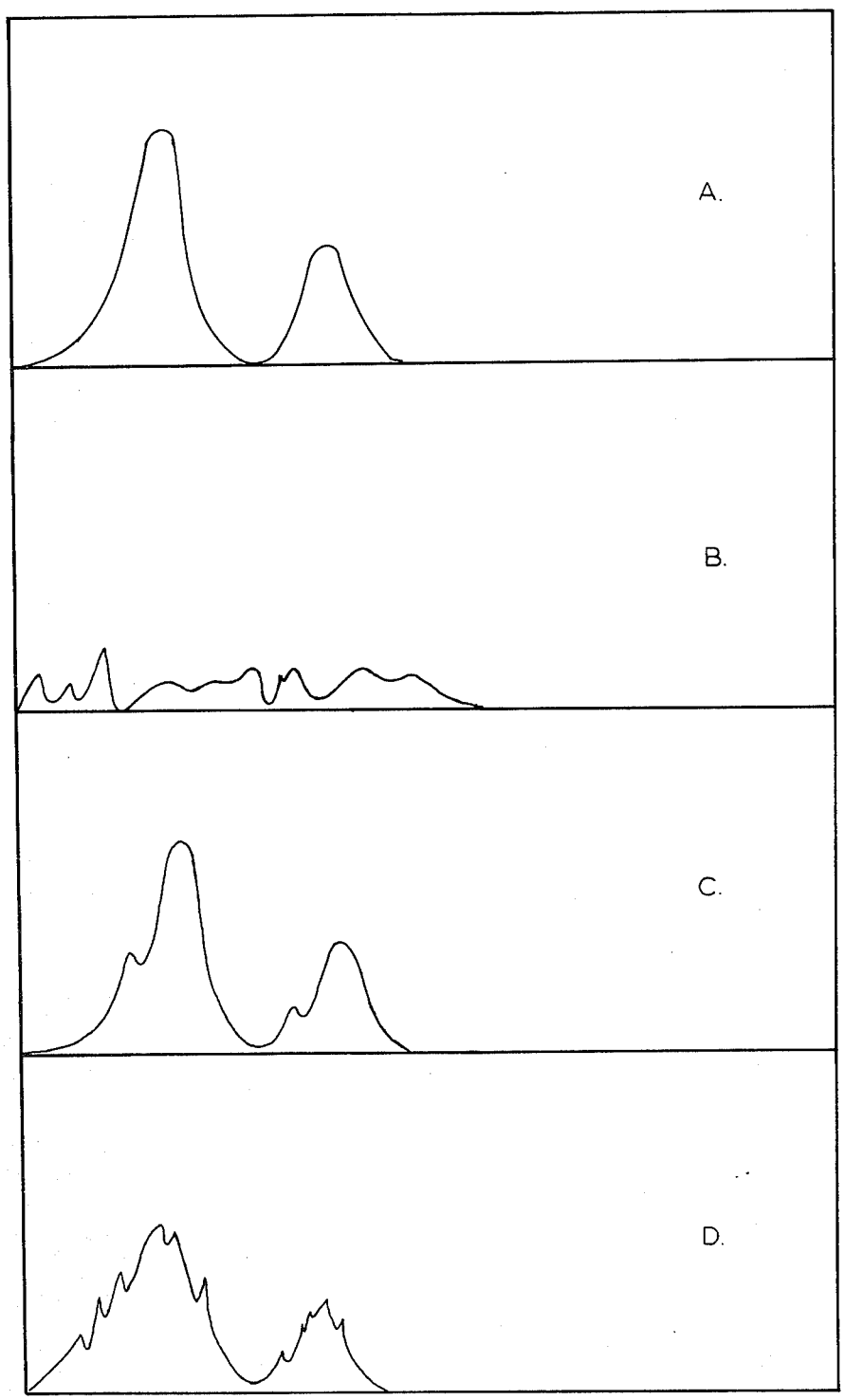
FIGS. 3a-3d are representative illustrations of oscilloscope displays for monocrystalline, amorphous and polycrystalline layers, which are generated by an ellipsometer system as shown in FIG. 2.

Information on the crystallinity of the film is immediately available by observation of the signal on the scope. If the film is monocrystalline, the signal presents two well-defined maxima as in FIG. 3a. If the film is amorphous the two maxima disappear leaving an erratic signal corresponding to noise as shown in FIG. 3b. A polycrystalline film produces a multiplicity of peaks centered around the two maxima observed in FIG. 3a. The number of peaks depends of the degree of crystallinity (i.e., the number of crystallites in the cross-section of the beam on the substrate). The observed signal varies from the shape shown in FIG. 3c, for two crystallites to the shape shown in FIG. 3d as the number of crystallites increases to finally become similar to the signal given by an amorphous layer (FIG. 3b).

Information on the thickness of the layer, for a monocrystalline film, can be obtained from the ratio of the amplitude of the two maxima of the signal under certain conditions. The position and amplitudes of these two maxima will depend on the orientation of the quarter wave plate in the source, on the thickness of the film and the orientation of the quarter wave plate in the analyzer. For a particular relationship between the orientation of the two quarter wave plates with respect to the plane of reflection on the substrate, the ratio of amplitudes of the two maxima will be a function of the thickness of the film. Consequently, the two quarter wave plates will have to be adjusted before proceeding with thickness measurement. This is most conveniently achieved by first removing the quarter wave plate on the analyzer side and rotating the one on the opposite side until a maximum is reached. The quarter wave plate is then fastened into that position. The return of the quarter wave plate in the analyzer side will produce two maxima on the screen. By rotating this plate on its axis one maximum will increase and the other will decrease until a maximum difference is reached. If the rotation is continued the greatest maximum starts to decrease as the smallest increases and passing through a position of equal amplitude they will reach a state of maximum difference, opposite to the one previously observed. This sequence is shown in FIG. 4 (a→b→c or vice versa).

If, by rotating the quarter wave plate on the analyzer side, the two maxima are adjusted to equal amplitudes, the growth of a film on the substrate will cause the two maxima to part from each other and the difference in amplitude will be proportional to the thickness of the film. Under these conditions, a maximum difference is reached for a thickness of the film equal to $\lambda/4$. If the film continues to grow, the maxima will return to a position of equal amplitude corresponding to a film thickness of $\lambda/2$ and further to another maximum difference for a film thickness of $3\lambda/4$ etc. A great accuracy can be achieved by adjusting the vertical amplifier of the oscilloscope in such a way that the maximum difference of amplitude corresponds to an even number of graduations on the screen (for example 10). In that case, each graduation will correspond to a thickness of the film of $\lambda/40$ (see FIG. 5).

According to the invention, the control of the crystalline growth (epitaxy) is effected by correcting the temperature at the surface of the substrate to fall within the ΔTe range. This can be accomplished by, for example, adjusting the electric current to heating electric coils surrounding the epitaxy oven within which the epitaxy substrate is located. This can be accomplished manually or automatically using the signals from the detection system of the ellipsometer system according to standard techniques. However, in view of speed of response and accuracy of the temperature adjustment to within the typically narrow temperature range of ΔTe, for example, about ±1° C. of Te, it is preferred to use an external means for heating the substrate surface. In accordance with a preferred embodiment the substrate temperature is maintained within the ΔTe range of the semiconductor material of the growing monocrystalline layer by means of an externally located infrared heat source coupled with appropriately located reflectors to direct the IR radiation to the substrate surface. The heating element of the IR heat source is electrically connected to the output of the photomultiplier or phototransistor detector of the ellipsometer whereby any detected deviations in epitaxial monocrystal formulation as a result of substrate surface temperatures outside the epitaxial temperature range i.e. Te±ΔTe, can be immediately corrected. For this purpose any suitable electronic circuit or microprocessor can be used. For example, a differential comparator circuit which can amplify the input pulses from the detector in proportion to deviations from a preset temperature to adjust the power fed to the infrared heat source has proven successful.

Figure 6:
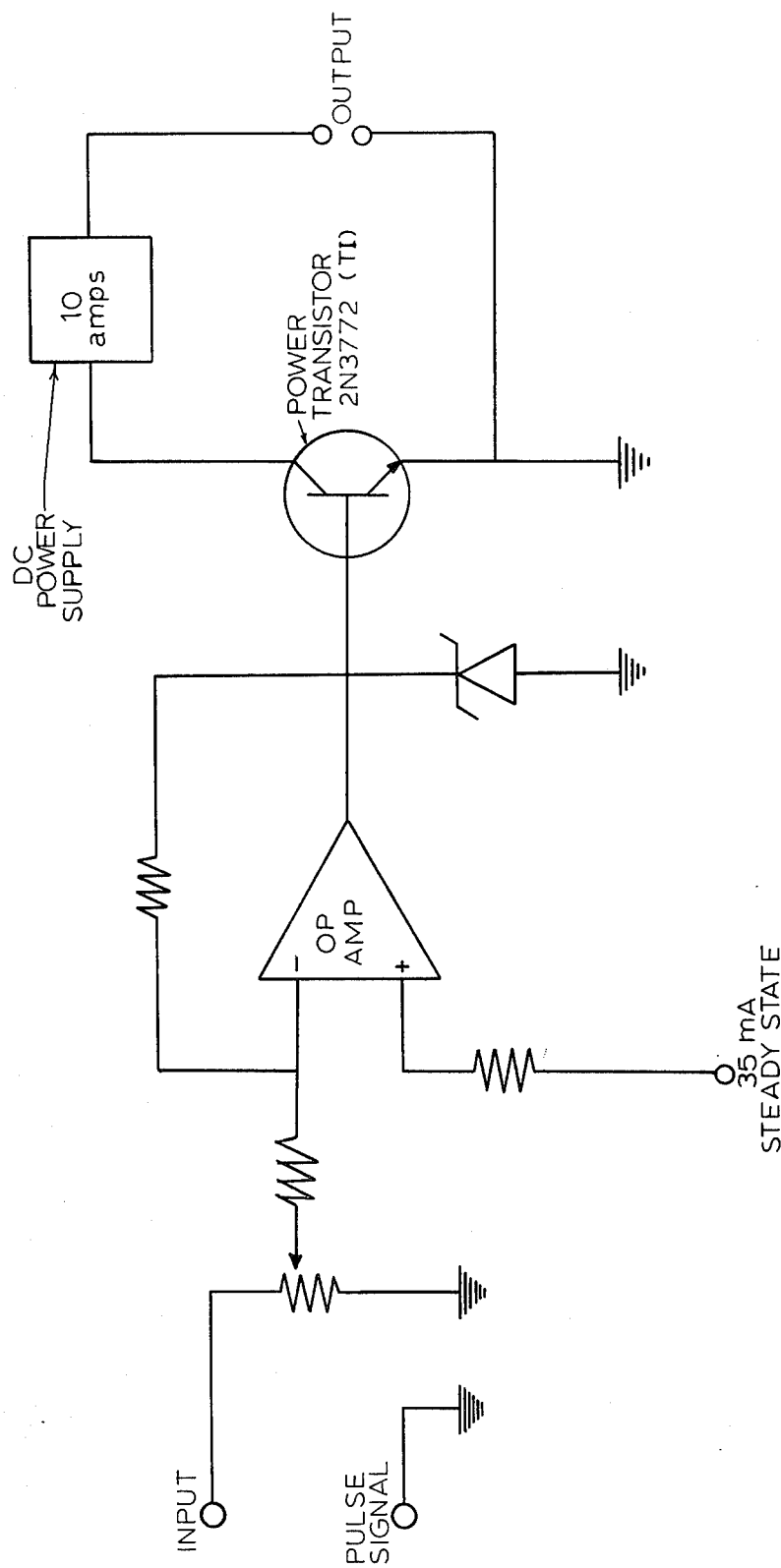
FIG. 6 is a circuit diagram of a differential comparator circuit which can be used in the present invention to control the epitaxial temperature.

FIG. 6 shows one particular differential comparator circuit which can be used in this invention to provide the temperature control needed for monocrystalline epitaxial growth. The input-pulse signal comes from the ellipsometer detector which will be either a phototransistor or photomultiplier as shown in FIG. 2. The output goes to the filament of an IR lamp which is the heat source for controlling the temperature at the surface of the epitaxial substrate.

The circuit illustrated in FIG. 6 will amplify a pulse which is more than 35 mV, to drive the IR source. For example, if the input signal is 35 mV in amplitude, then the output current will be about 4 amperes. If the input signal increases to 60 mV, then the output current will increase to 10 amperes.

The measurement and control of the thickness of the monocrystalline layer can be directly controlled by the output of the detection system of the ellipsometer by suitable electronic circuitry. This control can also be done manually by opening or closing the path of the atomic or molecular stream from the evaporation source to the epitaxial substrate in response to observations of the differential heights of the peaks observed on the oscilloscope as described above.

The single or multiple layer thin film monocrystalline structures of this invention, with or without additional doping, and with supporting structure can be used in such applications as interference layers in filters, light modulators and the like. However, the primary application of the semiconductor thin film monocrystalline structures is expected to be in photovoltaic solar cells. Accordingly, the invention will be described in detail in connection with the construction of solar cells using the thin film monocrystalline structures according to preferred embodiments of the invention.

The complex structure of a solar cell can be generated by depositing a single monocrystalline layer or a succession of individual monocrystalline layers of given electronic properties. Also, it is possible to form a single monocrystalline layer of gradually varying stoichiometry. These structures can be similar to the structure of red LED gallium arsenide base wafers which are formed by liquid epitaxy and have a GaAs silicon:N doped base layer and tellurium:N doped GaAsP upper layers of varying stoichiometry and a P(zinc) top layer.

Generally, the top layer will be formed with a band gap E which is transparent for the lower energy photons within the main absorption band of the base, e.g. GaAs, layer. In order to accomodate the various regions of the solar energy spectrum, it is preferred to cause a gradual variation of the stoichiometry of the upper layer, e.g. GaAsP, by controlling the evaporation rate of the elements together with the dopant; the band gap of the material in the several layers can be made to vary from 1.9 eV on the surface to 1.45 eV for GaAs at the interface with the base layer.

In the present invention, the building of the structure starts from an epitaxial substrate which will be subsequently removed (e.g. NaCl).

The first layer to be generated is the base layer (e.g. GaAs) with uniform stoichiometry and then the graded layer, which in this case is GaAsP. The operation is completed by the evaporation of a passive metal layer for the contact. After removing the device from the vacuum system the complex film structure is removed from the substrate and transferred onto a permanent mica or metal substrate.

Similar structures can also be generated using GaAlAs or other ternary compounds in order to match the conditions of use and optimize the energy conversion efficiency.

The advantages of a film structure are mainly:

1. Higher efficiency by limiting the thickness of the device to the active volume of the material that is the carrier diffusion length on each side of the junction interface. This decreases the series resistance of any portion of passive material in the structure.

2. Higher efficiency due to a better optical coupling between the radiant energy and the carrier generating material. The coupling and carrier generation efficiency is related to the graded band gap in the epitaxial layer and to a non-reflective type structure in the film.

3. Lower cost through a better use of the raw materials and a major decrease of the elementary steps leading to the manufacture of a cell.

The requirement for industrial production of large cells of $10^{19}$ mol/sec. on a surface of 100 cm$^2$ with an energy dispersion of less than 2/10 eV can be accomplished by this invention.

In order to achieve high efficiency cells three basic conditions are necessary:

a. A good lattice match (low $\delta$)
b. Doping level sufficient for a good P.N. junction
c. The stoichiometry in the layers must remain after the crystal growing process is completed.

The lattice match depends on the crystal structure of the various components of the heterostructure. The lattice mismatches for typical III–V compounds used for the following junctions are shown in Table 2.

TABLE 2

| Crystal | Lattice Constant | $\delta$ % |
|---------|------------------|------------|
| GaAs    | 5.646 Å          | 3          |
| GaP     | 5.447 Å          |            |
| GaAs    | 5.646 Å          | 0.12       |
| AlAs    | 5.639 Å          |            |
| GaAs    | 5.646 Å          | 0.22       |
| Ge      | 5.668 Å          |            |

The number of dislocations $n_d$ is a function of the lattice mismatch $\delta$: a $\delta$ of 3% corresponds to $n_d = 10^{10}$ cm$^{-2}$; 0.12% give $n_d = 10_8$ cm$^{31\ 2}$. A large density of dislocations is naturally detrimental to high efficiency. However, it has been found that with layer growth from the epitaxial base or function interface $\delta$ decreases and the layer seems to improve in perfection. The increase in perfection as the distance from the epitaxial substrate increases accounts for higher mobilities near the top surface of the structure.

The preparation of a thin film monocrystalline semiconductor structure will now be described including the preparation of the epitaxial substrate, the adjustment of the ellipsometer, evaporation and film growth doping and detachment of the film from the substrate. The preparation of a high efficiency solar cell from the semiconductor film will also be described.

a. Preparation of the substrate

The epitaxial substrate should be monocrystalline, and satisfy the following conditions:

(a) Same crystallographic system as the material of the film to be grown.

(b) Have a lattice constant within 10% of that of the material to be grown.

(c) The coefficients of expansion of the two materials, substrate and film, should match or nearly do so.

(d) After completion of the film, the substrate should be able to be separated from the film by dissolution or other means, without introducing undue stress to the film.

(e) The epitaxial surface on which the film will be deposited should correspond to one of the principal crystallographic planes of the substrate, preferably (111) or (100).

In the case of Ge or GaAs, an ideal substrate is sodium chloride: it matches the lattice constant, its expansion coefficient is close to one of the materials and it can be dissolved in water.

In the preparation of the substrate a fresh face is first cut (or cleaved) parallel to one of the planes (111) or (100). The orientation can be done with an x-ray goniometer with good accuracy. If the substrate crystal has been cleaved, the surface of cleavage can be used as such without further preparation. It is generally preferable to perform the operation of cleavage in vacuum. If the substrate crystal has been cut with a saw or other means, the surface has to be polished to an optical flatness. Crystals of NaCl already cut in the proper orientation and polished can be found on the market as infrared windows and it is economically advantageous to use such windows.

The polished surface of the substrate is generally coated with an amorphous layer (Belby layer) and therefore not suitable for epitaxy. This layer can be removed by ionic bombardment in the vacuum chamber.

The substrate is now "activated" and ready for epitaxial growth.

b. Adjusting the ellipsometer

After the activation of the substrate and its positioning into the epitaxial oven, the adjustment of the ellipsometer is initiated. First of all, before starting to evacuate the vacuum chamber, it should be ascertained that the ellipsometer beam is properly reflected by the surface of the substrate. Then, during the pumping cycle, the ellipsometer is adjusted through the following operations:

(a) Start the motor which produces the rotation of the polarizer in the analyzer section of the ellipsometer.

(b) Synchronize the oscilloscope scanning with the rotation of the polarizer.

(c) At this time, two maxima should be observed on the screen of the oscilloscope.

(d) Remove the quarter wave plate, $Q_2$, in the analyzer section so that only one maximum is observed on the screen.

(e) Bring the signal to maximum amplitude by rotating the quarter wave plate, $Q_1$, in the source section and block it in that position.

(f) Replace the quarter wave plate, $Q_2$, in the analyzer section.

(g) At this time, the two maxima reappear on the screen and can be alternately increased and decreased by rotating the quarter wave plate, $Q_2$, in the analyzer section.

Figures 4A, 4B, 4C:
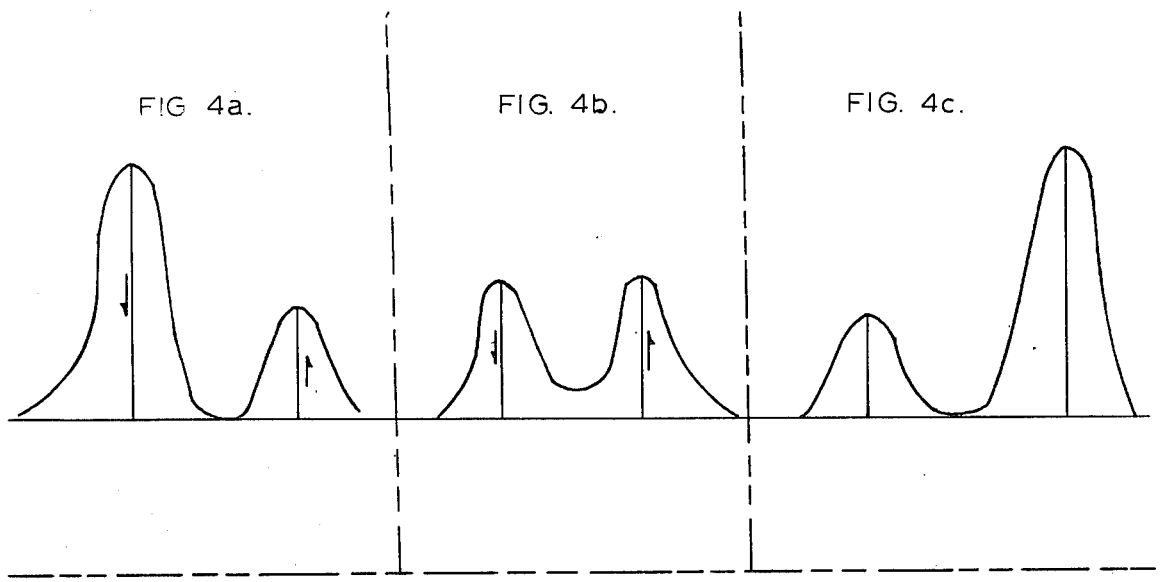
FIG. 4 is the sequence of oscilloscope views which will be observed in adjusting the ellipsometer for use in this invention.

(h) Rotate $Q_2$ until a maximum difference is observed (FIG. 4a or 4c).

Figure 5:
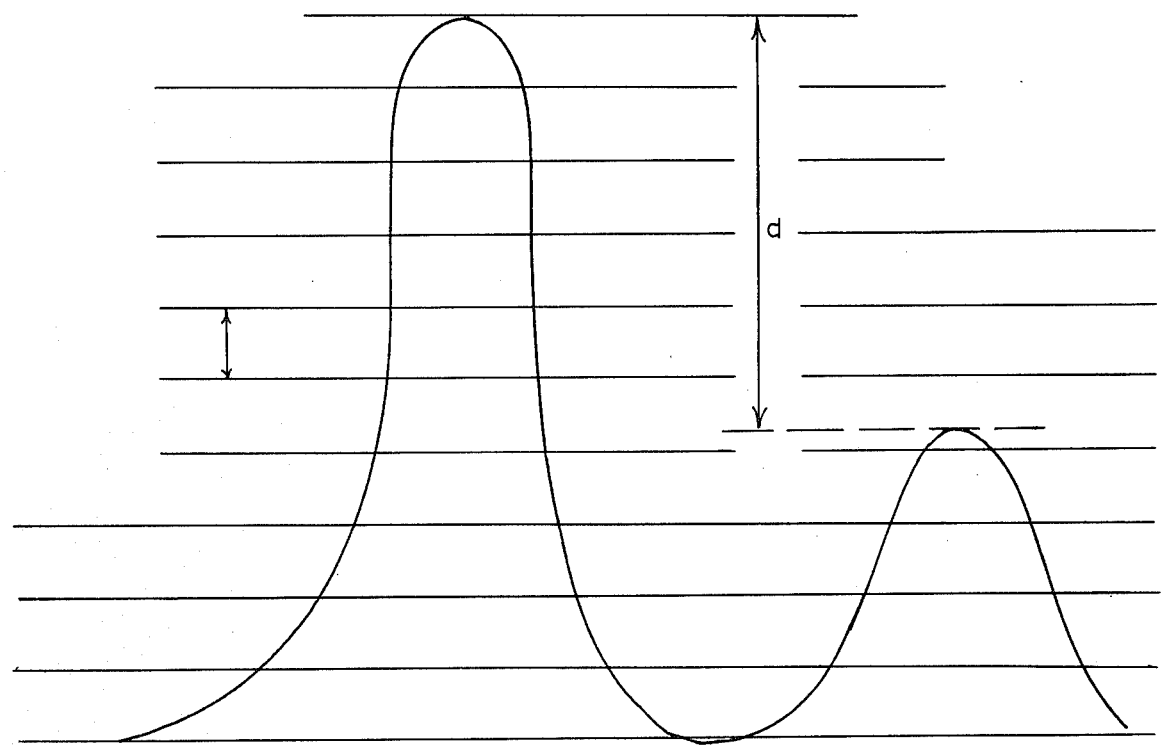
FIG. 5 is an illustration of an oscilloscope display according to a preferred arrangement of the ellipsometer system.

(i) Adjust the gain of the vertical amplifier on the scope in such a manner that the difference between the maxima corresponds to an even number (6 or 10) of graduations on the screen (FIG. 5).

(j) Rotate $Q_2$ to bring back the two maxima at the same level (FIG. 4b).

(k) The ellipsometer is now ready to control the growth of the film.

c. Evaporation and film growth

During the adjustment of the ellipsometer, the bell jar should be evacuated to a pressure of about $10^{-7}$ mm Hg. Also, the temperature of the epitaxial oven should be raised gradually to a temperature of about 500° C., as indicated by the thermocouple, 18. It should be noted that during the evaporation, the temperature at the surface of the substrate will be 20° to 30° higher than the oven's average temperature. The distance, h, between the crucible and substrate will generally be within the range of about 10 to 15 cm.

The evaporation will now take place through the following operations (see FIG. 7):

(a) Close the shutter, 20, (see FIG. 7), as to mask the aperture 25 in the epitaxial oven.

(b) Raise gradually the temperature of the crucible, 30, until the beginning of evaporation is observed on the wall of the quartz chimney, 32.

(c) At this time, open the shutter and observe the signal on the screen of the oscilloscope.

(d) If the two maxima weaken and disappear, close the shutter immediately, raise slightly the temperature in the epitaxial oven (5° to 10°), and open the shutter again.

(e) If the two maxima do not reappear, repeat (d) as many times as necessary to bring back these maxima.

(f) If the two maxima remain in (d) or after (e) proceed until the difference in maxima corresponds to the desired thickness.

(g) If the thickness is greater than $\lambda/4$ proceed through as many cycles as necessary, adding each time $\lambda/4$ (see FIG. 4).

(h) When the proper thickness has been reached, close the shutter and bring back the crucible and the epitaxial oven to room temperature. It is important not to break the vacuum and remove the substrate before returning to room temperature in the oven.

In the case of GaAs or other dissociable compounds, flash evaporation will be used. For this purpose, the crucible, 30, will remain empty and will be brought to a temperature above that of evaporation of GaAs. At this time, the shutter will be open and operation (e) above will proceed while small quantities of GaAs powder will be projected into the crucible from a special feeding device (not shown).

d. Doping

It could happen that, due to impurities existing in the material evaporated or brought into the film during the evaporation process, that a sufficient amount of structural defects will already exist in the film formed to provide enough sensitivity. But, this is not generally the case and, in order to obtain a controllable and optimum electronic behavior, doping will be necessary. For simplicity a film of germanium will be used as an example, but, of course, the same method can be applied to GaAs, GaP and other III–V compounds, as well as ternary material such as GaAlAs or GaAlP. Only the amounts and diffusion temperatures will be different.

In the doping process the amount of dopant necessary to provide the required density of vacancies will be deposited on the film and then, by increasing the temperature, it will be diffused into the film. Since the amount of dopant is too small to be controllable the dopant is not evaporated alone but in the form of an alloy with the film material. For example, if the film is 1000 Å thick, made of germanium and the dopant aluminum, the substrate surface being S =4.9 cm² ($\phi$=2.5), the total volume of the film will be:

$$v = s.\delta = 4.9 \times 10^{-5} \text{ cm}^3$$

with $\delta = 1000 \text{ Å} = 10^{-5}$ cm.

For a density of vacancies equal to $10^{18}/\text{cm}^3$ the total number of vacancies $N_v$ in the film should be:

$$N_v = 10^{18} v = 4.9 \times 10^{13}$$

If it is assumed that one atom of dopant will generate one vacancy the weight of dopant $P_{Al}$ nessary to provide this density of vacancies in the film is given by:

$$P_{Al} = N_v \times A_{Al} \times 10^{-23} = 4.9 \times 10^{13} \times 27 \times 10^{-23}$$
$$= 1.32 \times 10^{-8} \text{ gr}$$

where $A_{Al}$ is the atomic weight of aluminum.

To carry this amount of dopant in a layer of germanium 10 Å thick (for example), the amount of germanium $P_{Ge}$ will be:

$$P_{Ge} = s\delta\, p = 4.9 \times 10^{-7} \times 5.35 = 2.6 \times 10^{-6} \text{ gr}$$

where p = density of Ge in gr/cm³.

The percentage of aluminum $X_{Al}$ in the germanium alloy to evaporate from the crucible will be given by:

$$X_{Al} = 4\pi h^2 \delta p = 12.56 \times 10^2 \times 10^{-7} \times 5.35 = 6.7 \times 10^{-4} \text{ gr or } 0.67 \text{ m gr.}$$

h being the distance between the crucible and the substrate (for example h=10 cm).

Figure 9B:
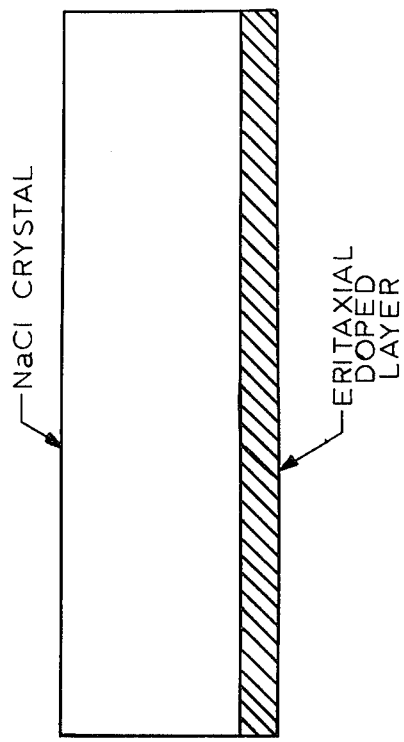
FIGS. 9a and 9b are, respectfully, schematic representations of the doping step of the invention before and after diffusion of the doping layer into the epitaxial layer.
Figure 9A:
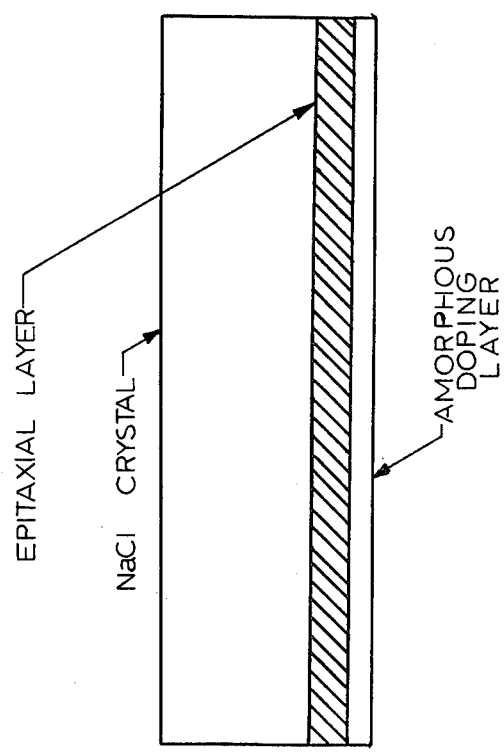

The various steps in the doping process can then be summarized as follows: (FIGS. 9 and 9b)

(a) Prepare the doping alloy with the epitaxial material and the dopant. Example: Ge+0.5% Al.

(b) Weigh the exact quantity of alloy necessary for doping and place it in a new crucible. Example: 0.67 mg of (Ge+0.5% Al).

(c) Evacuate the bell jar to $10^{-7}$ mm Hg.

(d) Start the ellipsometer which should still be adjusted as indicated above. At this time, the pattern on the oscilloscope should show two maxima.

(e) The substrate with the film being at room temperature, open the shutter 20 and heat the crucible, 30, to bright red until the total quantity of dopant is evaporated (one minute). The two maxima then disappear because of the formation of an amorphous layer Ge+Al.

(f) Close the shutter.

(g) Increase the temperature of the epitaxial oven to 350° C. and maintain this temperature until the two maxima reappear on the screen, which indicates that the amorphous layer has diffused into the crystalline film. Then, decrease the temperature of the oven gradually to room temperature. Again, it is important that the vacuum in the bell jar should not be broken until the oven is back to room temperature.

e. Detaching the film from the substrate

When the epitaxial oven is back to room temperature the substrate and the film can be removed from the vacuum chamber. The epitaxial film can then be separated from the substrate by immersion in a saturated solution of NaCl in water. The use of a solution of NaCl instead of water is preferred since the osmotic pressure developing at the interface NaCl - water would otherwise lead to stresses in the film and eventually destroy it.

To detach the film from its substrate, the sodium chloride crystal is firmly held by a pair of tweezers and introduced slowly into the NaCl solution at an angle of approximately 45°, the film then slides away from the substrate and remains floating at the surface of the liquid. The film is subsequently transported into pure distilled water to remove any trace of NaCl left on the layer. The film remains on the surface of the water until it is picked up on a special mica disc or any appropriate substrate.

Immediately after removing the film from the substrate, the film is transported into pure ethyl alcohol, then dried and stored in a desiccator until it is ready for use in the fabrication of a solar photovoltaic cell, or other end use.

The preparation of a photovoltaic solar cell can be accomplished, for example, by the following steps A–D.

A. The preparation of a p-n structure using the techniques described above.

B. The deposition of a contact structure on each side of the composite film.

C. Evaporation of an antireflection coating on top of the film structure or conditioning of the active structures to perform as antireflecting layers.

D. Packaging appropriate to the final use of the cell.

In the preparation of a p-n structure either of two alternatives can be used:

a. Epitaxial growth of the III–V compound on one side of the junction, evaporation of the p-dopant, diffusion of the dopant in the epitaxial layer, epitaxial growth of the III–V compound on the other side of the junction. evaporation of the n-dopant, diffusion of the dopant in the epitaxial layer.

b. Epitaxial growth of the entire junction structure by simultaneous sublimation of the III–V compound and the dopants, starting with the p-dopant and switching to the n-dopant at the junction interface.

The contact structure can be similar to those used for standard solar cells, e.g., evaporated metal grid structure, lead wires and ohmic contact on the n region. Alternatively, the adherence and contact of the film structure onto a metal evaporated on a mica disc or a metal disc can be used.

The unsupported film structure as it results from the process of this invention is particularly appropriate to the design of an antireflection structure by itself, thus providing the maximum exchange of the radiant energy in the active parts of the structure. This will allow the structure of the cell itself to be adapted to that of an antireflecting composite layer. It is also possible to provide the classical antireflection coating on top of the active structure by well known techniques.

Figure 11:
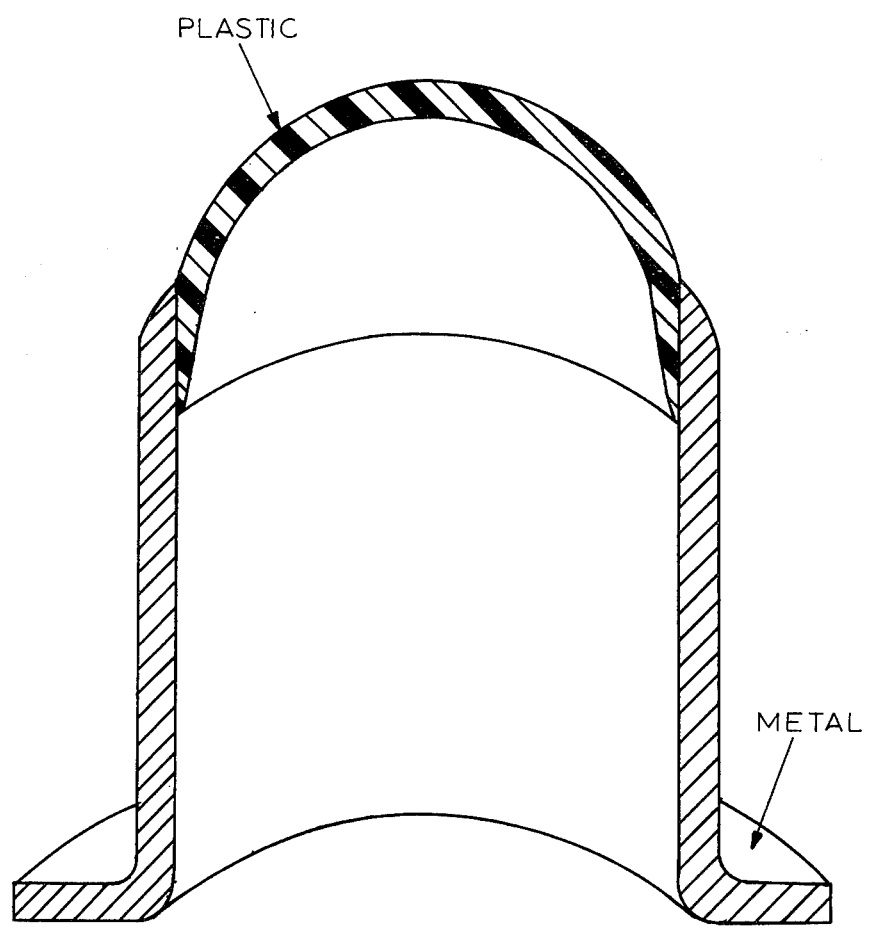
Figure 12:
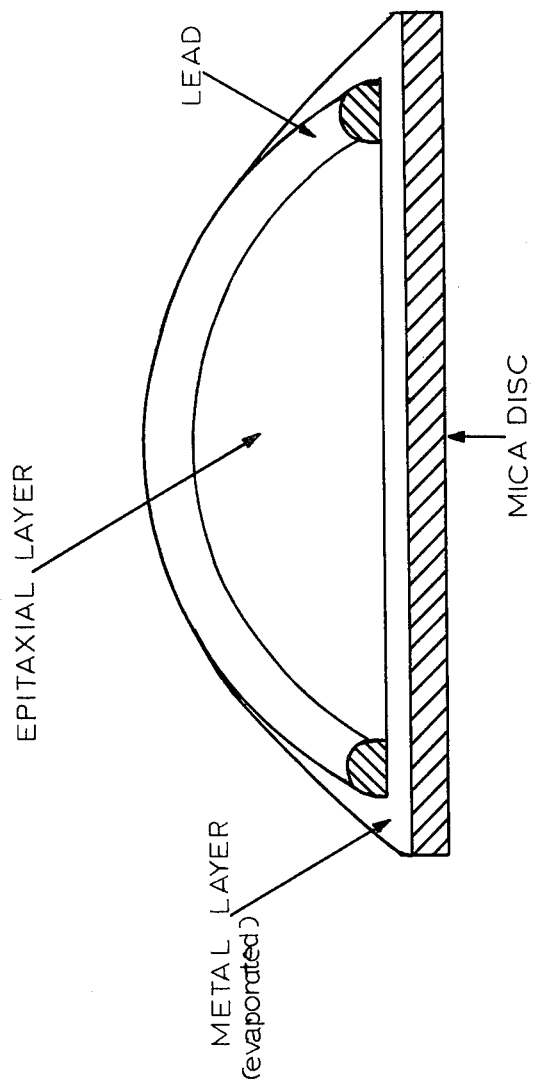

The packaging of the cell will depend on the application. The cells can be used individually in a design similar to a transistor header, as shown in FIG. 10. In this design the mica disc supporting the film is mounted on the two leads of the base and the cap is terminated with a window or lens which can be used as a concentrator. To take advantage of a 27° solid angle on the surface of the film a spherical or parabolic window can also be considered (FIG. 11). When the cell is to be integrated on a large panel it is preferable to use it directly as it is on the flat mica or metal substrate with proper mounting of the contact structure on the periphery of the substrate (FIG. 12).

Figure 7:
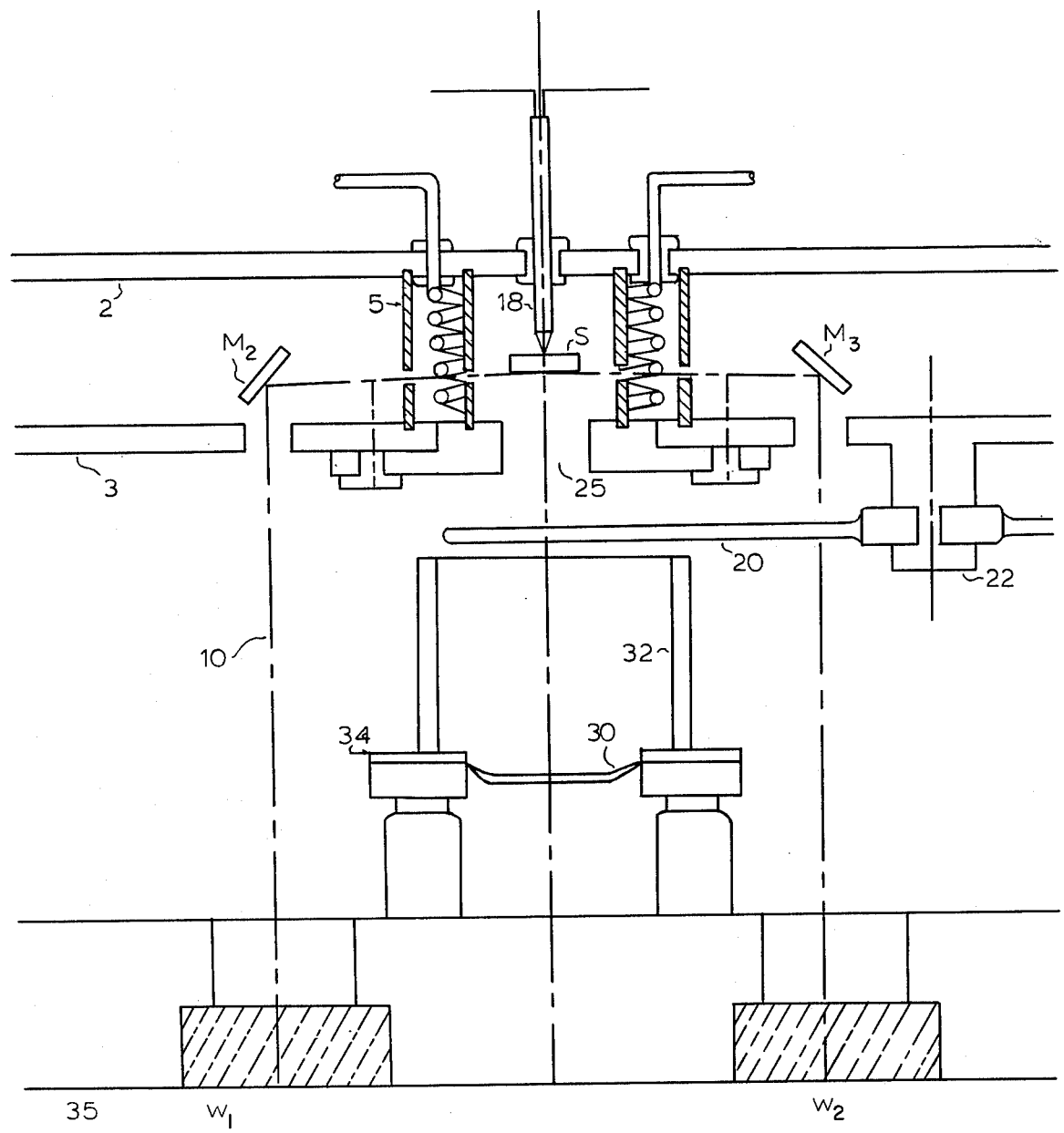
FIG. 7 is a schematic cross-sectional view of the vacuum chamber thermal vapor deposition apparatus used in the present invention.

In the process of this invention, the epitaxial growth is performed in a vacuum. A suitable system for this purpose will include a standard evaporating unit having at least an 18" bell jar which can be pumped down to $10^{-7}$ mm Hg. The inner part of the vacuum chamber as shown in FIG. 7 includes the following components:

(a) Two platforms 2, 3 supported by four columns (not shown) for holding various fixtures involved in the crystal growing technique.

(b) A substrate oven 5 mounted on the lower platform 3.

(c) Two optical mirrors $M_2, M_3$ for the reflection of the laser beam 10 on the substrate S in the oven.

(d) A Japanese fan shutter 20 mounted on the lower plate and guided externally by a small Alnico magnet 22.

(e) An evaporation source of variable shape with appropriate material feeding according to the semiconductor utilized.

(f) A high voltage electrode 34 for the cleaning of the components in the jar by electrical discharge.

(g) Optical windows $W_1$, $W_2$ in the base plate 35 for the incoming and outgoing of the laser beam.

(h) Various electrical feedthrough or electrodes (not shown) as needed.

(i) Parabolic reflectors $R_3$, $R_4$ for directing the infrared radiation from an external source onto the surface of the substrate S.

Figure 8:
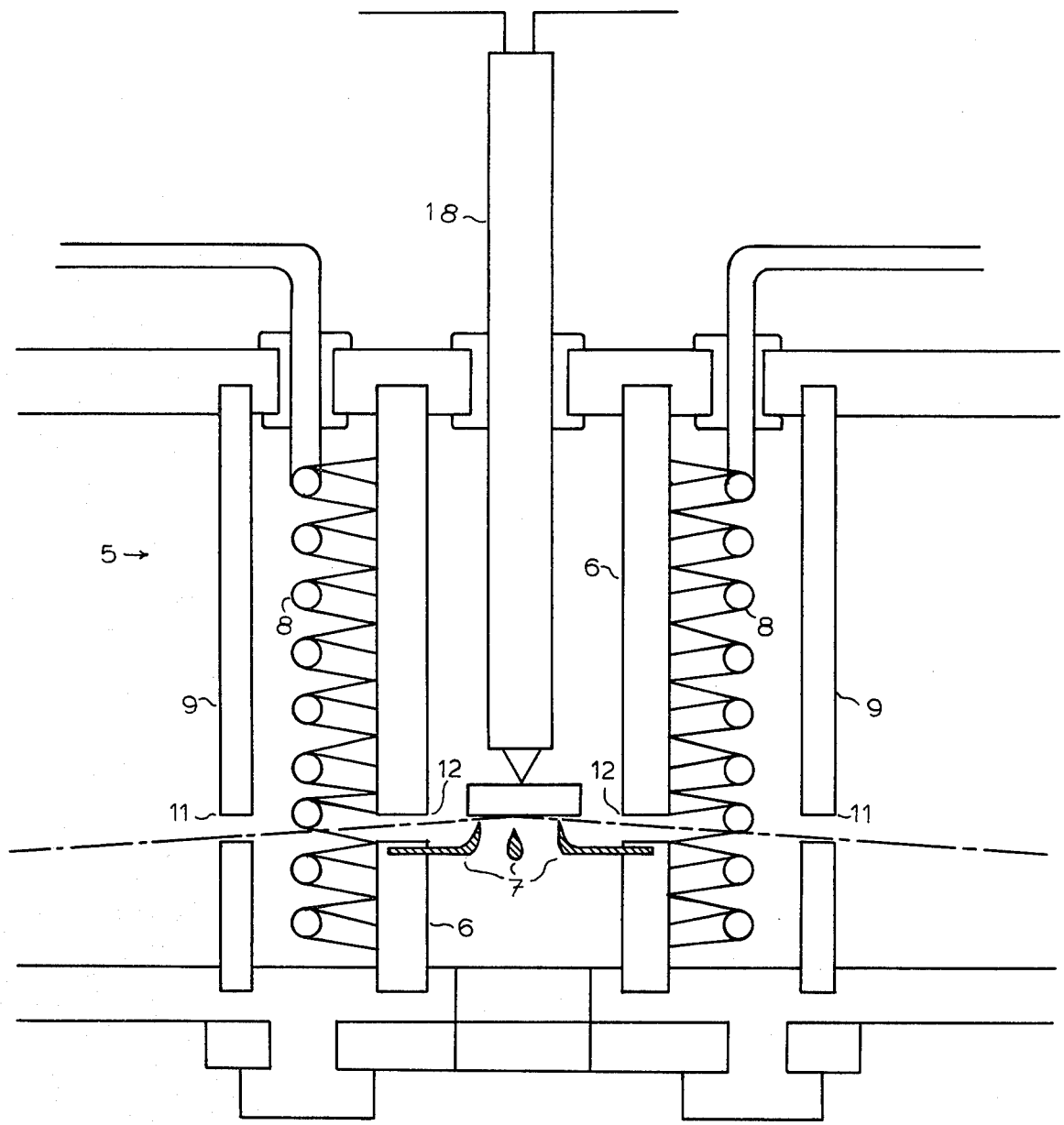
FIG. 8 is an enlarged schematic side elevation view of the substrate oven shown in FIG. 7.

The substrate oven is used to bring the substrate at the epitaxial temperature and keep an isothermal distribution of this temperature over the surface of the substrate. The oven is shown in greater detail in FIG. 8.

The oven has a black body configuration providing an equilibrium of the energy generated in the oven's chamber. It is made of a quartz cylinder 6 supporting the substrate on three tungsten pins 7, surrounded by a tungsten coil 8 generating the heat, the ensemble being enclosed in a tantalum shield 9. Two holes 11, 12 are provided in the tantalum shield and in the quartz cylinder to allow the ellipsometer beam to strike on the surface of the substrate during the film-growing process. The angle between the substrate and the ellipsometer beam should be under 5° for maximum efficiency. A thermocouple 18 introduced from the top of the tantalum cylinder is brought in contact with the upper part of the substrate.

Various types of evaporation crucibles can be used for forming semiconductor epitaxial films according to this invention. The crucible material will be selected according to the epitaxial material to be evaporated. The following table 3 indicates the type of source to use for a variety of materials:

TABLE 3

| Epitaxial Material | Crucible Material | Mode of Evaporation |
|---|---|---|
| Ge | W | Direct |
| Si | BeO, C | Direct |
| GaAs | Ta | Flash |
| InAs | Ta | Flash |
| InSb | Ta | Direct |
| $SnO_2$ | Ta | Direct |
| $TiO_2$ | Ta | Flash |
| $SiO_2$ | Ta | Flash |

TABLE 3-continued

| Epitaxial Material | Crucible Material | Mode of Evaporation |
|---|---|---|
| $CeO_2$ | Pt | Direct |
| Al | W | Direct |
| Au | W, Ta | Direct |

The crucibles can be made in the form of boats or crucibles from sheets of W, Ta, Mo or Pt or wire of the same materials. Boats will generally be more convenient to use with a powder.

The evaporation of compounds requires flash evaporation which is obtained by projecting small quantities of the material to evaporate in a boat heated at the temperature of evaporation. This mode of evaporation is utilized for materials that would decompose prior to reaching the temperature of evaporation, such as GaAs, InAs, $TiO_2$ and $SiO_2$.

Where monocrystalline layers of more than one semiconductor material are to be deposited, or where the stoichiometry of a binary or ternary semiconductor monocrystalline layer is to be varied gradually (or incrementally) several different approaches can be used, depending, generally, on whether or not the evaporation or sublimation temperature of the semiconductor is less than or greater than its dissociation temperature.

In the case where Tdiss > Tsubl, several crucible sources can be used, one for each of the constituent elements of the binary or ternary semiconductor. The temperature in each crucible can be adjusted to vary the rates of evaporation of the elements in each crucible to control the ratios of the respective elements reaching the epitaxial substrate where the corresponding compound forms in situ.

Alternatively, incremental or continuously varying stoichiometry can be achieved based on flash evaporation of different alloys of the desired semiconductor materials in the order in which the layers are to be deposited. Since the variation in composition of the respective layers will be only minor the epitaxial temperature will be the same or nearly so for each layer. Therefore, the critical factor will be the selection of an appropriate epitaxial substrate according to the criteria discussed above.

In the present invention substantially any semiconductor material can be grown by epitaxy. However, preferred semiconductors for photovoltaic cells include those based on gallium, such as gallium arsenides, gallium phosphides, gallium aluminum arsenide and gallium aluminum phosphides.

What I claim is:

1. In a process for preparing a thin film semiconductor of one or more monocrystalline layers of a semiconductor material in an evacuated chamber by epitaxial growth by vapor deposition of at least one monocrystalline layer on an epitaxial substrate, the improvement comprising continuously simultaneously controlling the crystallinity and measuring the thickness of each epitaxial monocrystalline layer during the growth thereof by directing an elliptically polarized beam of light at a low angle of incidence over the surface of the epitaxial substrate where the monocrystalline layer is growing, feeding the reflected beam of light to an analyzer to detect any variation in ellipticity of the reflected beam as a function of the crystallinity and film thickness and controlling the vapor deposition in response to any detected variation until the desired crystallinity and thickness is obtained.

2. The process of claim 1 wherein a laser beam is used as the source of the elliptically polarized beam of light.

3. The process of claims 1 or 2 which further comprises the steps of cooling the epitaxial film and substrate to room temperature, depositing an amorphous layer of a dopant on a monocrystalline layer, and raising the temperature of the epitaxial film and substrate to a temperature which allows the dopant to diffuse into said monocrystalline layer.

4. The process of claim 3 wherein the amorphous layer comprises the dopant, in that amount which will provide a predetermined density of active defects, as a mixture or as an alloy with the material of the monocrystalline layer.

5. The process of claim 1 which further comprises the step of separating the thin film semiconductor from the epitaxial substrate.

6. The process of claim 1 which comprises forming a plurality of monocrystalline layers of binary or ternary semiconductor materials on the epitaxial substrate wherein the stoichiometry of the layers is gradually varied by controlling the evaporation rate and order of vaporization of the constituent elements of the semiconductor materials wherein each resulting layer has a band gap responding to a different wavelength of the electromagnetic spectrum varying from the longest wavelength at the bottom layer to the shortest wavelength at the top layer.

7. The process of claim 1 or 6 wherein the semiconductor material comprises a binary semiconductor.

8. The process of claim 7 wherein said binary semiconductor comprises gallium arsenide or gallium phosphide or mixtures thereof.

9. The process of claim 1 or 6 wherein the semiconductor material comprises a ternary semiconductor.

10. The process of claim 9 wherein the ternary semiconductor comprises gallium aluminum phosphide or gallium aluminum arsenide or mixtures thereof.

* * * * *